United States Patent
Luchini (10) Patent No.: US 10,145,782 B2
(45) Date of Patent: Dec. 4, 2018

(54) MECHANICAL TESTING APPARATUS

(71) Applicant: The Boeing Company, Chicago, IL (US)

(72) Inventor: Timothy John Franklin Luchini, St. Louis, MO (US)

(73) Assignee: The Boeing Company, Chicago, IL (US)

(*) Notice: Subject to any disclaimer, the term of this patent is extended or adjusted under 35 U.S.C. 154(b) by 197 days.

(21) Appl. No.: 15/350,691

(22) Filed: Nov. 14, 2016

(65) Prior Publication Data

US 2018/0136112 A1    May 17, 2018

(51) Int. Cl.
  *G01N 19/02*  (2006.01)
  *G01N 19/04*  (2006.01)
  *G01N 33/00*  (2006.01)

(52) U.S. Cl.
  CPC .......... *G01N 19/02* (2013.01); *G01N 19/04* (2013.01); *G01N 33/00* (2013.01); *G01N 2033/0003* (2013.01); *G01N 2203/0025* (2013.01); *G01N 2203/0037* (2013.01)

(58) Field of Classification Search
  CPC ............... G01N 19/02; G01N 19/04; G01N 2033/0003; G01N 2203/0021; G01N 2203/0025; G01N 2203/0037

USPC ......... 73/7, 9, 788, 841, 843, 847, 856, 858, 73/866
See application file for complete search history.

(56) References Cited

U.S. PATENT DOCUMENTS

| 4,936,135 A * | 6/1990 | Annis ................... G01N 3/56 73/7 |
| 4,938,055 A * | 7/1990 | Tsuda ................... G01N 3/56 73/146 |
| 2011/0303018 A1* | 12/2011 | de Bondt ............. G01N 3/56 73/760 |

OTHER PUBLICATIONS

Long, "Composites forming technologies," 1st Edition, Woodhead Publishing Limited and CRC Press LLC., copyright 2007, 345 pages.
Erland et al., Inter and Intra-Ply Shearing of Uncured Carbon Fibre Laminates, ECCM16—16th European Conference on Composite Materials, Seville, Spain, Jun. 2014, 8 pages.

* cited by examiner

*Primary Examiner* — Benjamin Schmitt
(74) *Attorney, Agent, or Firm* — Yee & Associates, P.C.

(57) ABSTRACT

The mechanical testing apparatus comprises a wheel and a platform. The wheel is configured to hold a first specimen and rotate relative to a second specimen to apply torque to the second specimen using the first specimen. The platform is biased towards the wheel and configured to hold the second specimen.

20 Claims, 9 Drawing Sheets

MECHANICAL TESTING APPARATUS

BACKGROUND INFORMATION

1. Field

The present disclosure relates generally to mechanical testing of materials. Yet more specifically, the present disclosure includes a mechanical testing apparatus that may obtain mechanical property characterization of materials by applying torque.

2. Background

Mechanical property characterization may provide modeling inputs for manufacturing operations, including composite forming operations, or quantified data related to production needs. Accurate and repeatable mechanical property testing is desirable for building reliable process models for manufacturing operations.

Currently, process models for composite forming operations use numerous material and process characterization inputs to analyze the resulting composite structure. Desirable parameters for composite forming process models include fabric locking angle, intra-ply shear, inter-ply slipping/friction, and ply bending. Although testing approaches exist for each of these parameters, the testing approaches have not been standardized. Further, the inter-ply properties may be difficult to measure. Mechanical property characterization techniques do not characterize prepreg slippage across tools, inter-ply sliding, or dynamic slipping/sliding measurement.

Forming operations and other manufacturing operations for composite materials are commonly designed by practicing the art. Composite parts are produced and then tested until composite parts with desirable properties are formed. Current material characterization approaches and methods may limit the ability to understand the manufacturing operations from process models.

Once a forming operation and material type have been selected, many of the processing costs have also been selected without knowing what the costs are. A testing apparatus would help to generate data, allowing for informed decisions and conclusions to be made. Simple and rapid testing approaches are needed in order to support the manufacturing environment where design guidelines and process analysis are desired. Therefore, it would be desirable to have a method and apparatus that takes into account at least some of the process variables discussed above, as well as other possible questions.

SUMMARY

In one illustrative embodiment, a mechanical testing apparatus is presented. The mechanical testing apparatus comprises a wheel and a platform. The wheel is configured to hold a first specimen and rotate relative to a second specimen to apply torque to the second specimen using the first specimen. The platform is biased towards the wheel and configured to hold the second specimen.

In another illustrative embodiment, a mechanical testing method is presented. A first specimen is secured to a wheel of a mechanical testing apparatus. A second specimen is secured to a platform of the mechanical testing apparatus, wherein the platform is biased towards the wheel. The wheel is rotated relative to the second specimen to apply torque to the second specimen using the first specimen.

In yet another illustrative embodiment, a system is presented. The system comprises a mechanical testing apparatus, a first specimen, and a second specimen. The mechanical testing apparatus comprises a wheel, a motor, a platform, and a number of sensors. The motor is connected to the wheel and configured to apply a rotational force to the wheel. The platform is biased towards the wheel by a biasing member. The number of sensors is configured to measure at least one of temperature, torque, linear translation, rotational translation, or applied load. The first specimen is secured to the wheel of the mechanical testing apparatus. The second specimen is secured to the platform of the mechanical testing apparatus.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account one or more different considerations. For example, the illustrative embodiments recognize and take into account that composite materials are light-weight, high performance, materials created by combining two or more functional components. For example, a composite material may include reinforcing fibers bound in a polymer resin matrix. The fibers may be unidirectional or may take the form of a woven cloth or a fabric. The fibers and resins are arranged and cured or consolidated to form a composite material.

In manufacturing composite structures, layers of composite material are formed. When layers are unidirectional, each unidirectional layer of the composite structure has a respective fiber direction within the layer. A layup for the composite structure includes the quantity of layers, the respective fiber directions, and the order of the layers within the composite structure. A layup may have a plurality of different fiber directions.

The layers may be comprised of fibers in sheets. In some cases, resin may be infused or preimpregnated into the sheets. These types of sheets are commonly referred to as prepreg.

The different illustrative embodiments recognize and take into account that one goal is to provide a way to measure the coefficient of friction between plies during a forming process. The different illustrative embodiments recognize and take into account that the presentation of a consistent method to measure off-axis measurements would be a significant advancement in itself.

The different illustrative embodiments recognize and take into account that it would be efficient to measure the static and dynamic coefficient of friction between plies in a single test under a single set up. The different illustrative embodiments also recognize and take into account that it would be an advantage to measure the coefficient of friction between plies during a forming process. The different illustrative embodiments recognize and take into account the desire to measure off-axis measurements. The different illustrative embodiments further recognize and take into account a desire to measure more robust data inputs than the double lap shear tests. The different illustrative embodiments recognize and take into account that it is desirable to measure the coefficient of static friction, as well as the dynamic friction, as multiple plies begin to slide against each other. The different illustrative embodiments recognize and take into account that it is desirable to understand the addition of heat to measure the changing viscosity of the matrix and fiber together.

The state of the art approach is the double lap shear test. However, this test tends to be cross sectionally dependent and the contact area is constantly changing during the test. Additionally, the test is undesirable when looking at how off-axis plies interact with each other. There is no standard testing approach for evaluating an interface mechanism. There are many solutions to find inputs. However, each of the solutions are unidirectional tests. There are also qualitative comparisons.

The proposed apparatus would be able to desirably control for tack, shear, and sliding friction, and discern the effect of these properties on forming. All significant variables for inter-ply properties could be controlled including temperature, rate sensitivity, fiber orientation, ply angle, normal load/pressure, compaction, and dynamic versus static tack have on forming.

The presented apparatus is a new fixture for variable controlled tack, shear, and sliding friction. Variables for the presented apparatus include at least one of: temperature, rate, fiber orientation, ply angle, load/pressure, compaction, or dynamic versus static tack.

Figure 1:
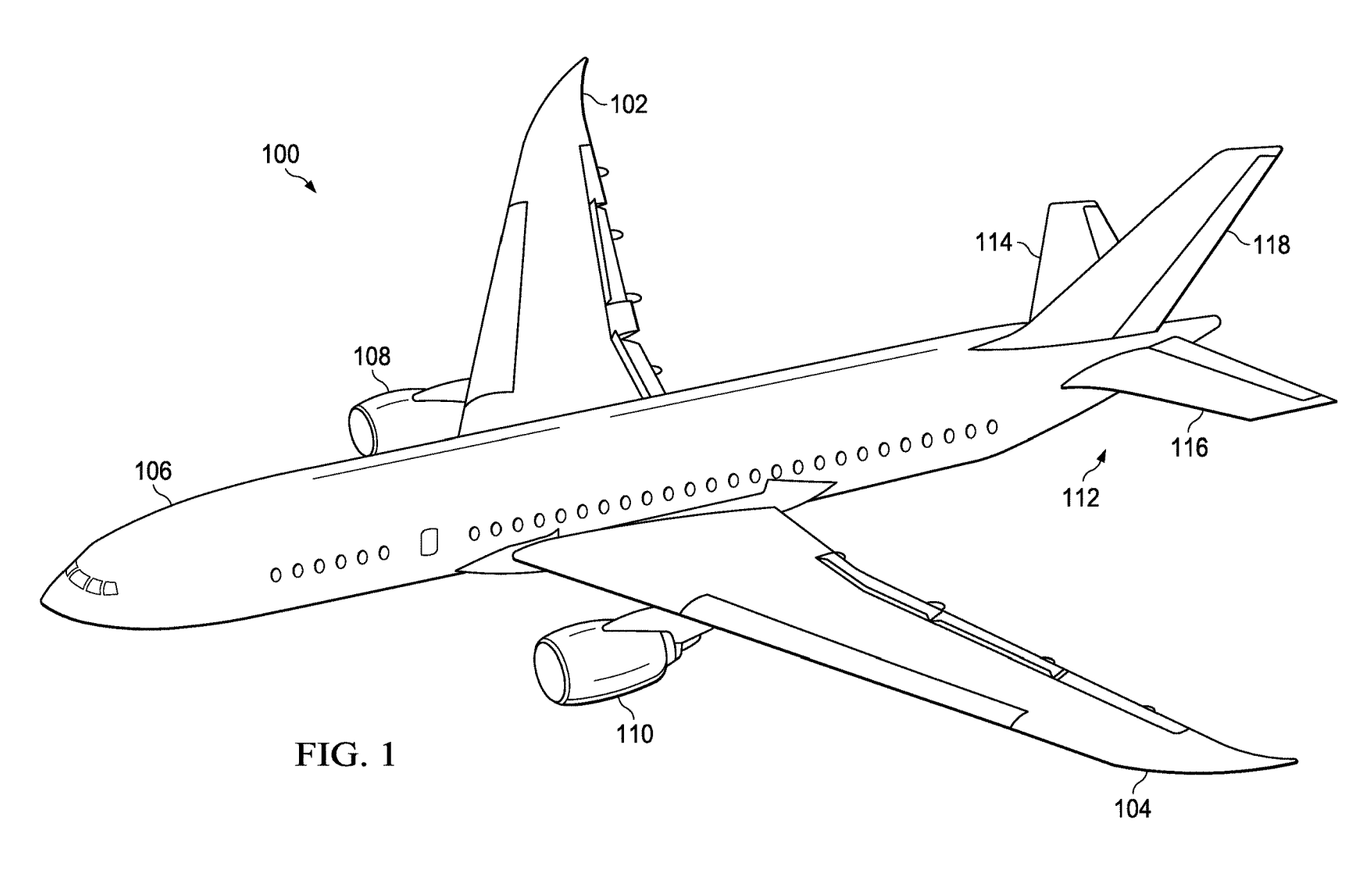
FIG. 1 is an illustration of an aircraft in which an illustrative embodiment may be implemented.

Referring now to the figures, and in particular, with reference to FIG. 1, an illustration of an aircraft is depicted in which an illustrative embodiment may be implemented. In this illustrative example, aircraft 100 has wing 102 and wing 104 attached to body 106. Aircraft 100 includes engine 108 attached to wing 102 and engine 110 attached to wing 104.

Body 106 has tail section 112. Horizontal stabilizer 114, horizontal stabilizer 116, and vertical stabilizer 118 are attached to tail section 112 of body 106.

Aircraft 100 is an example of an aircraft having materials tested using a mechanical testing apparatus. For example, aircraft 100 is an example of an aircraft having composite materials tested using a mechanical testing apparatus as described in at least one of wing 102, wing 104, or body 106. Aircraft 100 is an example of an aircraft designed using characterized material data determined using a mechanical testing apparatus as described.

As used herein, the phrase "at least one of," when used with a list of items, means different combinations of one or more of the listed items may be used, and only one of each item in the list may be needed. In other words, "at least one of" means any combination of items or number of items may be used from the list, but not all of the items in the list are required. The item may be a particular object, a thing, or a category.

For example, "at least one of item A, item B, or item C" may include, without limitation, item A, item A and item B, or item B. This example also may include item A, item B, and item C or item B and item C. Of course, any combination of these items may be present. In other examples, "at least one of" may be, for example, without limitation, two of item A, one of item B, and ten of item C; four of item B and seven of item C; or other suitable combinations.

This illustration of aircraft 100 is provided for purposes of illustrating one environment in which the different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, a rotorcraft, or other suitable type of aircraft.

Although the illustrative examples for an illustrative embodiment are described with respect to an aircraft, an illustrative embodiment may be applied to other types of monuments. The monument may be, for example, a mobile structure, a stationary structure, a land-based structure, an aquatic-based structure, or a space-based structure. More specifically, the monument may be a surface ship, a tank, a personnel carrier, a train, a spacecraft, a space station, a satellite, a submarine, a manufacturing facility, a building, or other suitable types of structures. Further the monument may be a portion of any desirable structure.

Figure 2:
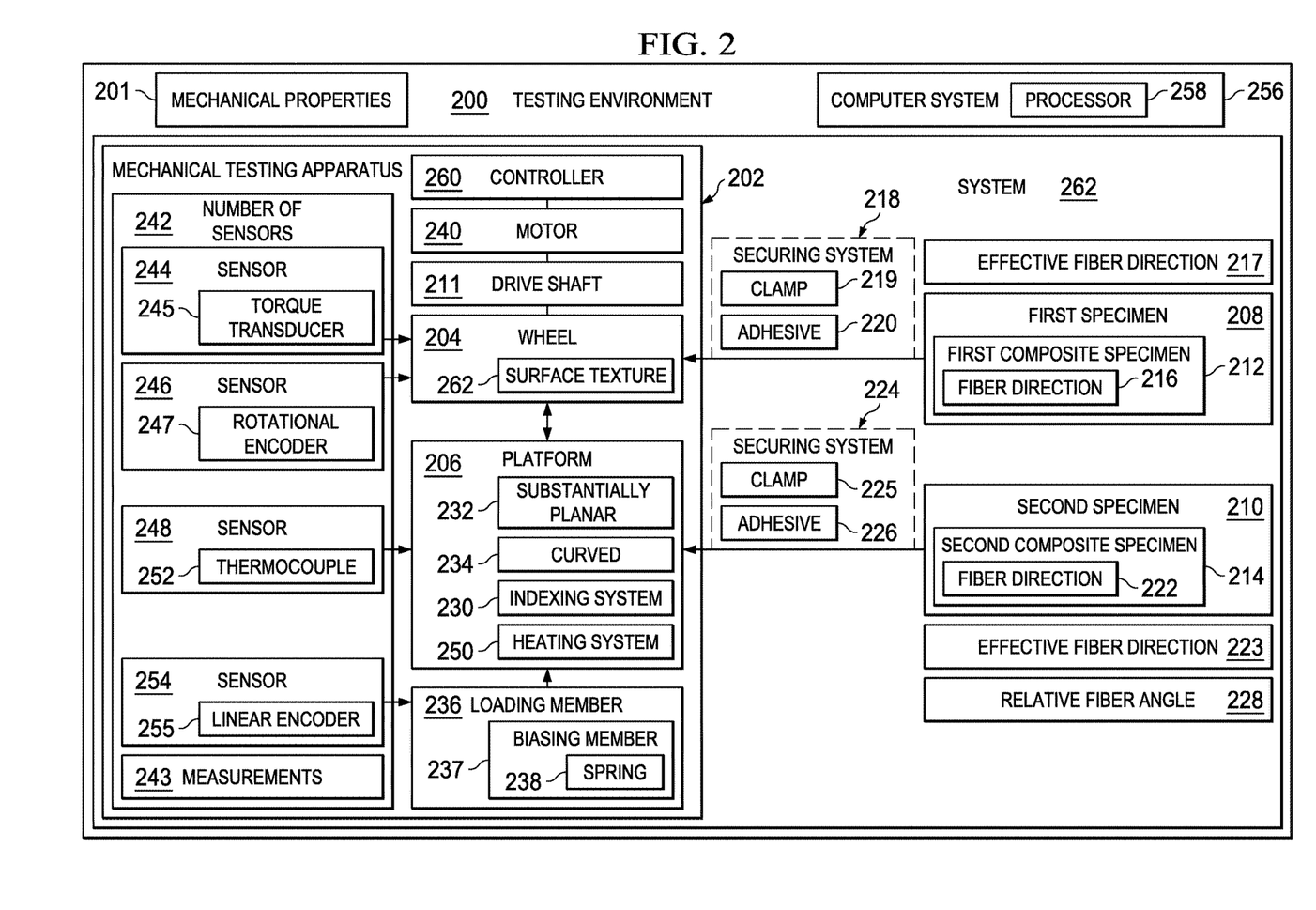
FIG. 2 is an illustration of a block diagram of a testing environment including a mechanical testing apparatus in accordance with an illustrative embodiment.

Turning now to FIG. 2, an illustration of a block diagram of a testing environment including a mechanical testing apparatus is depicted in accordance with an illustrative embodiment. Testing environment 200 is an environment for testing materials such as materials forming aircraft 100 of FIG. 1. For example, mechanical properties of composite materials used to form aircraft 100 may be determined in testing environment 200.

Mechanical properties 201 may be determined using mechanical testing apparatus 202 of testing environment 200. Mechanical testing apparatus 202 comprises wheel 204 and platform 206. Wheel 204 is configured to hold first specimen 208 and rotate relative to second specimen 210 to apply torque to second specimen 210 using first specimen 208. Platform 206 is biased towards wheel 204 and configured to hold second specimen 210.

Mechanical testing apparatus 202 may be described as an inter-ply property testing fixture. Mechanical testing apparatus 202 takes advantage of a rotational torque instead of a linear tensile force application.

In some illustrative examples, wheel 204 is an interchangeable wheel. When wheel 204 is an interchangeable wheel, wheel 204 may be replaced by a wheel of any desirable material or size. When wheel 204 is an interchangeable wheel, wheel 204 may be removed and replaced so that another specimen may be tested. When wheel 204 is an interchangeable wheel, time between tests may be reduced. When wheel 204 is interchangeable, first specimen 208 may be secured to wheel 204 when wheel 204 is not secured to drive shaft 211 of mechanical testing apparatus 202.

Wheel 204 is formed from any desirable material. Wheel 204 is formed from a material having sufficient strength to reduce undesirable deformation of wheel 204 during testing of first specimen 208 and second specimen 210. Deformation of wheel 204 during testing may be described as a "footprint." The size and shape of the "footprint" of wheel 204 during testing is taken into account in determining mechanical properties 201 of first specimen 208 and second specimen 210. In some illustrative examples, wheel 204 may be formed of a metal, such as a steel. In other illustrative examples, wheel 204 may be formed of a polymeric material, such as a rubber.

First specimen 208 and second specimen 210 may be formed from any desirable material. In some examples, first specimen 208 and second specimen 210 may be formed from different materials. The materials for first specimen 208 and second specimen 210 may be selected from composites, ceramics, polymeric materials, or any other directional materials to be tested.

In some illustrative examples, first specimen 208 and second specimen 210 are composite specimens. When first specimen 208 is a composite specimen, first specimen 208 may be referred to as first composite specimen 212. When second specimen 210 is a composite specimen, second specimen 210 may be referred to as second composite specimen 214.

First composite specimen 212 may include any quantity of plies. Second composite specimen 214 may include any quantity of plies. In some illustrative examples, first composite specimen 212 and second composite specimen 214 each includes only a single respective ply. When first composite specimen 212 and second composite specimen 214 each includes only one ply, interactions are between only the material characteristics of first composite specimen 212 and second composite specimen 214. Thus, mechanical properties 201 are the interaction of the single plies at the interface between first specimen 208 and second specimen 210.

When at least one of first composite specimen 212 and second composite specimen 214 have multiple plies, the effect of the multiple plies in series influences measurements 243. For example, multiple plies of first composite specimen 212 would interact with each other during testing. As another example, multiple plies of second composite specimen 214 would interact with each other during testing. Thus, mechanical properties 201 are the interaction of first specimen 208 against second specimen 210 as well as any interactions within at least one of first specimen 208 or second specimen 210.

First composite specimen 212 has fiber direction 216 relative to edges of first composite specimen 212. Fiber direction 216 is set during creation of first composite specimen 212. The fibers of first composite specimen 212 are laid with fiber direction 216. Fiber direction 216 may be any desirable direction. Frequently used fiber directions in composites may include zero degrees, thirty degrees, forty-five degrees, sixty degrees, or ninety degrees.

In mechanical testing apparatus 202, fiber direction 216 of first composite specimen 212 will desirably be zero degrees. First composite specimen 212 will be wrapped around wheel 204 and indexed relative to wheel 204. Fiber direction 216 will be in line with the load application direction of wheel 204.

The position of first composite specimen 212 within mechanical testing apparatus 202 creates effective fiber direction 217. For example, when fiber direction 216 of first specimen 208 is zero degrees, first specimen 208 may be in line with load application of wheel 204, and wheel 204 may be positioned such that the angle of the fibers of first specimen 208 is approximately thirty degrees relative to the edges of platform 206. Thus, by positioning wheel 204 to position first specimen 208, effective fiber direction 217 of first specimen 208 is set. Effective fiber direction 217 of first specimen 208 may be altered by changing the position of first specimen 208 within mechanical testing apparatus 202.

In some illustrative examples, effective fiber direction 217 and fiber direction 216 are the same. In other illustrative examples, effective fiber direction 217 and fiber direction 216 are different.

Securing system 218 holds at least a portion of first specimen 208 on a portion of wheel 204. In some illustrative examples, securing system 218 holds all of first specimen 208 on wheel 204. In other illustrative examples, only a portion of first specimen 208 is secured to wheel 204 by securing system 218. In these illustrative examples, a portion of first specimen 208 is loose. The loose portion of first specimen 208 is held taut against wheel 204 as wheel 204 rotates. In these illustrative examples, first specimen 208 is self-tightening. There would be no slipping as wheel 204 rotates due to the applied torque of wheel 204.

Securing system 218 includes at least one of clamp 219 or adhesive 220, or any desirable securing apparatus. In some illustrative examples, first specimen 208 is associated with wheel 204 by at least one of clamp 219 or adhesive 220.

Second composite specimen 214 has fiber direction 222 relative to edges of second composite specimen 214. Fiber direction 222 is set during creation of second composite specimen 214. The fibers of second composite specimen 214 are laid with fiber direction 222. Fiber direction 222 may be any desirable direction.

The position of second composite specimen 214 within mechanical testing apparatus 202 creates effective fiber direction 223. For example, when fiber direction 222 of second composite specimen 214 is 0 degrees, second composite specimen 214 may be held on platform 206 such that the angle of the fibers of second composite specimen 214 is approximately 30 degrees relative to the edges of platform 206. Thus, by positioning second composite specimen 214, effective fiber direction 223 of second composite specimen 214 is set. Effective fiber direction 223 of second composite specimen 214 may be altered by changing the position of second composite specimen 214 within mechanical testing apparatus 202.

In some illustrative examples, effective fiber direction 223 and fiber direction 222 are the same. In other illustrative examples, effective fiber direction 223 and fiber direction 222 are different.

Securing system 224 holds at least a portion of second specimen 210 on platform 206. Securing system 224 includes at least one of clamp 225 or adhesive 226, or any desirable securing apparatus. In some illustrative examples, second specimen 210 is associated with platform 206 by at least one of a clamp 225 or adhesive 226. In some illustrative examples, securing system 224 takes the form of a picture frame clamping system including clamp 225.

Relative fiber angle 228 is an angle between effective fiber direction 217 and effective fiber direction 223. Relative fiber angle 228 is changed by changing at least one of effective fiber direction 217 or effective fiber direction 223.

Mechanical testing apparatus 202 includes indexing system 230 associated with platform 206. Effective fiber direction 223 is set by indexing second composite specimen 214 to indexing system 230. Indexing system 230 may include markings for identifying effective fiber direction 223. Relative fiber angle 228 of second specimen 210 relative to first specimen 208 is set using indexing system 230.

First specimen 208 and second specimen 210 may be formed from any desirable material. Mechanical testing apparatus 202 may be used to test any materials that may slide or move relative to each other. For example, at least one of first specimen 208 or second specimen 210 may be sand paper, vinyl, or any other desirable material that moves relative to another layer of material.

Platform 206 may take any desirable form. In some illustrative examples, platform 206 is substantially planar 232. In other illustrative examples, platform 206 is curved 234.

Loading member 236 applies a load onto platform 206 towards wheel 204. In some illustrative examples, loading member 236 make take the form of biasing member 237. Biasing member 237 biases platform 206 towards wheel 204. Loading member 236 includes any desirable form of load source. The load source may also be referred to as a normal load source. The load source of loading member 236 may include biasing member 237, a pneumatic force, a mechanical motor, a linear actuator, a threaded rod, or any other desirable form of force applicator. In some illustrative examples, loading member 236 includes biasing member 237 in the form of spring 238.

As loading member 236 biases platform 206 towards wheel 204, motor 240 rotates wheel 204 relative to platform 206. Motor 240 rotates wheel 204 relative to platform 206 while second specimen 210 is secured to platform 206 and first specimen 208 is secured to wheel 204. By rotating wheel 204 while platform 206 is biased towards wheel 204, torque is applied to second specimen 210 using first specimen 208.

Mechanical testing apparatus 202 also includes number of sensors 242 to take measurements 243 during operation of mechanical testing apparatus 202. As used herein, "a number of" when used with reference to items means one or more items. Thus, number of sensors 242 includes one or more sensors.

Number of sensors 242 may include any desirable quantity or type of sensors. In some illustrative examples, number of sensors 242 includes sensor 244 associated with wheel 204 and is configured to measure torque. In some illustrative examples, sensor 244 is torque transducer 245.

Torque transducer 245 measures torque. The torque may be plotted against time to determine a static friction coefficient ($\mu_s$) and a kinetic friction coefficient ($\mu_k$). Mechanical properties 201 include the static friction coefficient ($\mu_s$), the kinetic friction coefficient ($\mu_k$), and tack.

A static coefficient of friction is still friction or rolling friction. One example of a static coefficient of friction is the friction of the rolling resistance of a wheel as the wheel rolls against a flat surface. The kinetic coefficient of friction is sliding friction of two surfaces past each other. One example of a kinetic coefficient of friction is the friction of a wheel sliding across a surface when a car slams on its brakes.

The static friction coefficient ($\mu_s$) or kinetic friction coefficient ($\mu_k$) is related to applied force (F) through normal force (N). In mechanical testing apparatus 202, the torque is equivalent to applied force (F) times moment arm (R) of wheel 204. Torque transducer 245 of mechanical testing apparatus 202 measures torque and converts to friction through prescribing the radius of wheel 204 and the normal force.

The static friction coefficient ($\mu_s$) and kinetic friction coefficient ($\mu_k$) are determined based on the output from sensor 244 measuring torque, such as torque transducer 245. As motor 240 begins to apply torque, sensor 244 will read an increasing torque. Once wheel 204 begins to slide relative to platform 206, the static coefficient of friction will be represented by the peak of the torque versus time plot. Once the torque application begins to reach steady state the dynamic coefficient of friction will be plotted versus time. These two inputs are used for the inputs into forming models or design guidelines.

In some illustrative examples, number of sensors 242 includes sensor 246 associated with wheel 204 and is configured to measure rotation of wheel 204. In some illustrative examples, sensor 246 is rotational encoder 247.

In some illustrative examples, number of sensors 242 includes sensor 248 configured to measure the temperature of platform 206. Heating system 250 may be associated with platform 206 to control the temperature of second specimen 210 during testing. By applying heat using heating system 250, interactions of first specimen 208 and second specimen 210 may be measured at a controlled temperature. The temperature may include ambient temperature, operating temperatures, processing temperatures, or any other desirable temperatures. In some illustrative examples, sensor 248 is thermocouple 252.

In some illustrative examples, number of sensors 242 includes sensor 254 configured to measure the movement of platform 206. Sensor 254 may be configured to measure the displacement of platform 206 relative to wheel 204. In some illustrative examples, sensor 254 is linear encoder 255.

Measurements 243 from number of sensors 242 are used to determine mechanical properties 201. Computer system 256 with processor 258 analyzes measurements 243 to determine mechanical properties 201. Mechanical properties 201 may include interply properties between first specimen 208 and second specimen 210. Mechanical properties 201 may include at least one of intra-ply shear, inter-ply slipping/friction, or ply bending.

Controller 260 controls operation of mechanical testing apparatus 202. For example, controller 260 may actuate motor 240. In some illustrative examples, controller 260 may also control loading member 236.

The illustration of testing environment 200 in FIG. 2 is not meant to imply physical or architectural limitations to the manner in which an illustrative embodiment may be implemented. Other components, in addition to or in place of the ones illustrated, may be used. Some components may be unnecessary. Also, the blocks are presented to illustrate some functional components. One or more of these blocks may be combined, divided, or combined and divided into different blocks when implemented in an illustrative embodiment.

For example, wheel 204 may optionally include surface texture 262. Surface texture 262 may be added to wheel 204 to provide additional friction between wheel 204 and first specimen 208. Surface texture 262 may be added using any desirable method such as material deposition, mechanical abrasion, or chemical abrasion.

As another example, mechanical testing apparatus 202, first specimen 208, and second specimen 210 may be described as components of system 264. System 264 comprises mechanical testing apparatus 202 comprising wheel 204, motor 240 connected to wheel 204 and configured to apply a rotational force to wheel 204, platform 206 biased towards wheel 204 by biasing member 237, and number of sensors 242 configured to measure at least one of a temperature, a torque, a linear translation, a rotational translation, or an applied load. System 262 also comprises first specimen 208 secured to wheel 204 of mechanical testing apparatus 202, and second specimen 210 secured to platform 206 of mechanical testing apparatus 202.

Figure 3:
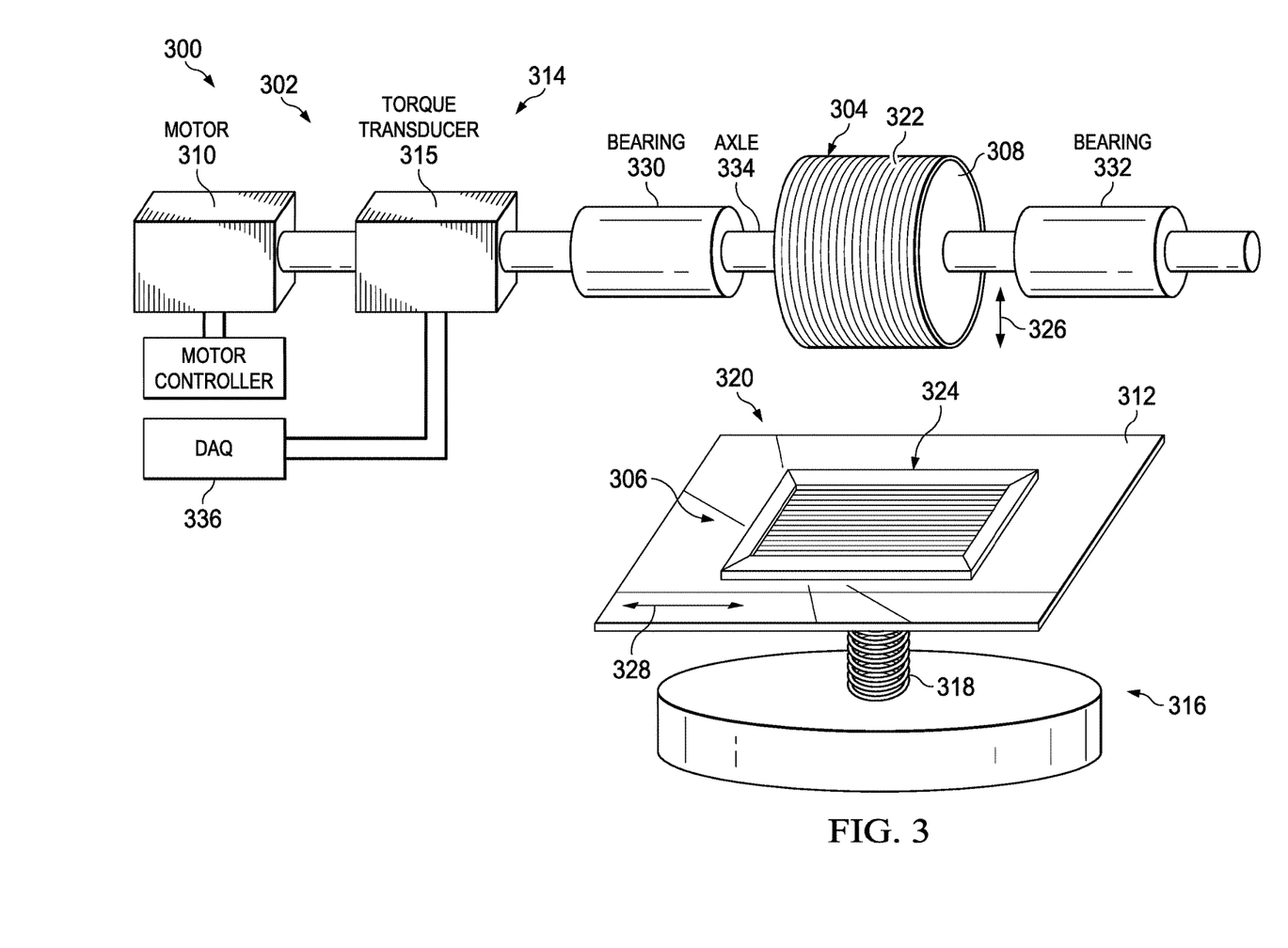
FIG. 3 is an illustration of a mechanical testing apparatus in accordance with an illustrative embodiment.

Turning now to FIG. 3, an illustration of a system including a mechanical testing apparatus is depicted in accordance with an illustrative embodiment. System 300 includes mechanical testing apparatus 302, first specimen 304, and second specimen 306. Mechanical testing apparatus 302 is a physical implementation of mechanical testing apparatus 202 of FIG. 2.

Mechanical testing apparatus 302 comprises wheel 308, motor 310, platform 312, and number of sensors 314. Motor 310 is connected to wheel 308 and configured to apply a rotational force to wheel 308. Platform 312 is biased towards wheel 308 by biasing member 316. As depicted, biasing member 316 is spring 318. Number of sensors 314 is configured to measure at least one of a temperature, a torque, a linear translation, a rotational translation, or an applied load. As depicted, number of sensors 314 includes torque transducer 315. Torque transducer 315 measures torque applied to second specimen 306 using first specimen 304.

First specimen 304 is secured to wheel 308 of mechanical testing apparatus 302. Second specimen 306 is secured to platform 312 of mechanical testing apparatus 302. Second specimen 306 is indexed on platform 312 using indexing system 320. As depicted, first specimen 304 is first composite specimen 322 and second specimen 306 is second composite specimen 324. As depicted, first composite specimen 322 has a zero-degree fiber direction. As depicted, second composite specimen 324 has a zero-degree fiber direction. Relative fiber direction 326 of second composite specimen 324 relative to first composite specimen 322 is set using index system 320. As depicted, relative fiber direction 326 is ninety degrees.

Effective fiber direction 328 of second specimen 306 is a result of indexing of second specimen 306 relative to platform 312. As depicted, effective fiber direction 328 is zero degrees. Effective fiber direction 328 of second specimen 306 can be changed by changing how second specimen 306 is indexed relative to platform 312.

FIG. 3 also includes additional representative components, such as axles, controllers, and bearings. These depictions are only representative and not limiting as to number, type, or location.

For example, bearings may be used in system 300 to provide low friction in reference to the inter-ply frictions. Bearings may be used in any desirable location of system 300 and may be any desirable type of bearing. For example, the bearings may be low friction, sealed, race bearings or low friction Teflon bearings depending on the temperature requirements. Depending on budget, magnetic bearings might be present. As depicted, system 300 includes bearing 330 and bearing 332 associated with axle 334.

As another example, FIG. 3 includes DAQ 336. DAQ 336 may represent a data acquisition unit. The data acquisition unit is used for obtaining and organizing the data from any sensors associated with system 300. For example, DAQ 336 may obtain and organize the data from torque transducer 315. Further, DAQ 336 may obtain and organize the data from any other sensors such as thermocouples, an encoder, or a load cell.

Figure 4:
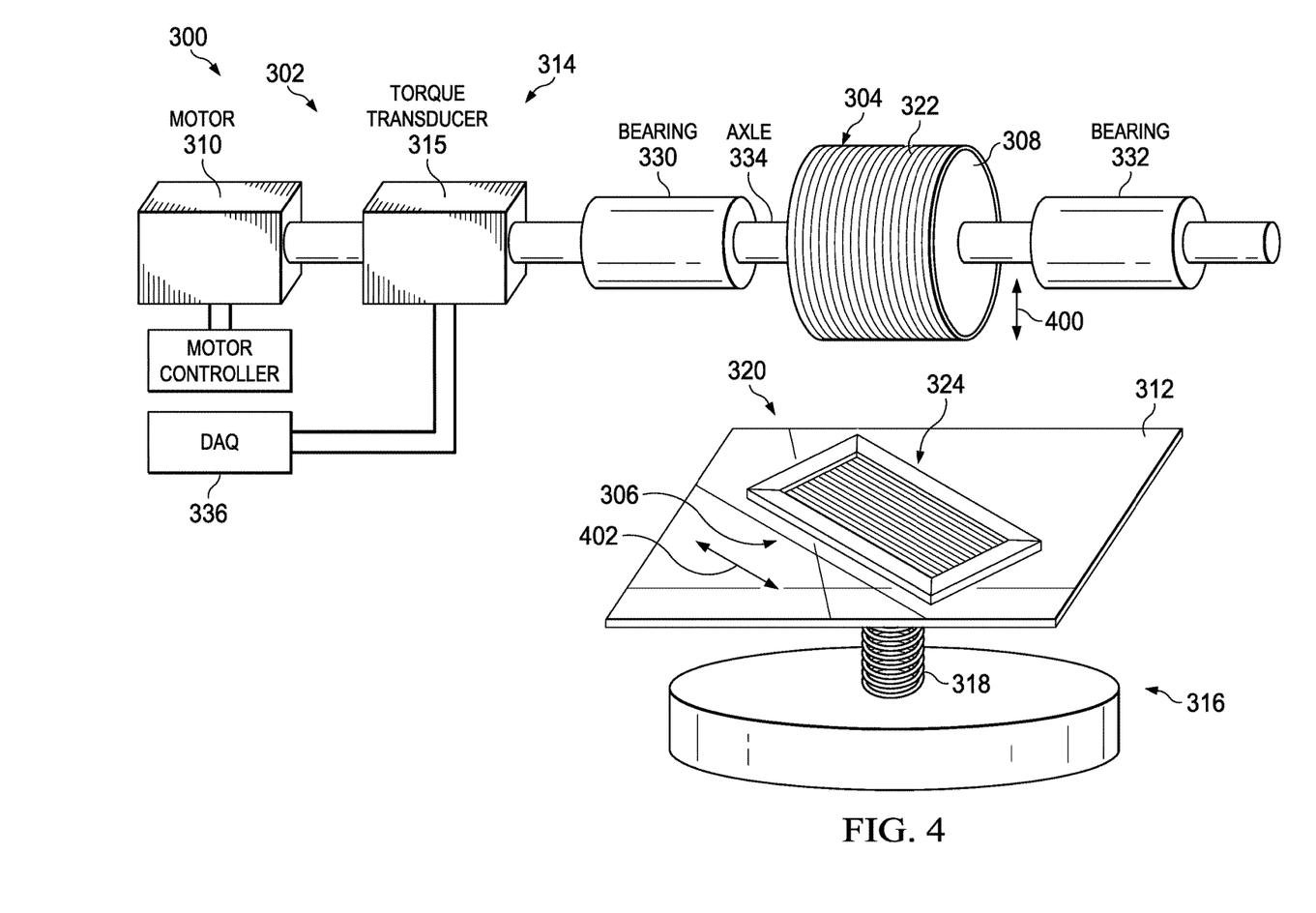
FIG. 4 is an illustration of a mechanical testing apparatus with a specimen having a fiber direction angled relative to the platform in accordance with an illustrative embodiment.

Turning now to FIG. 4, an illustration of a mechanical testing apparatus with a specimen having a fiber direction angled relative to the platform is depicted in accordance with an illustrative embodiment. In FIG. 4, second specimen 306 has been rotated on platform 312. Effective fiber direction 400 was changed from effective fiber direction 328 of FIG. 3 by changing how second specimen 306 was indexed relative to platform 312.

As depicted, effective fiber direction 400 is approximately thirty degrees. Thus, relative fiber direction 402 of second specimen 306 relative to first specimen 304 is approximately 60 degrees. Second specimen 306 may be indexed relative to platform 312 such that any desirable effective fiber direction is created.

Figure 5:
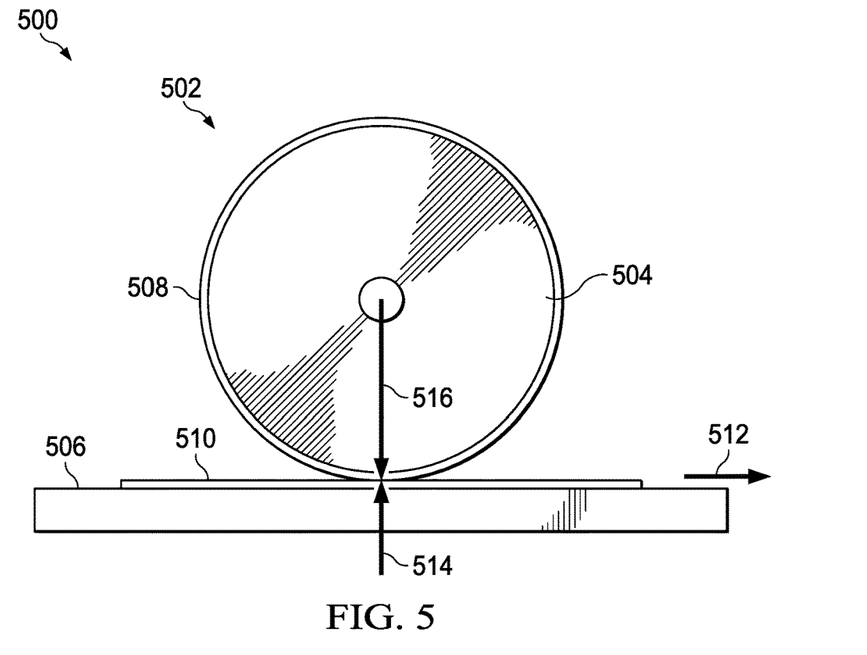
FIG. 5 is an illustration of a simplified side view of a mechanical testing apparatus with a first specimen around a wheel in accordance with an illustrative embodiment.

Turning now to FIG. 5, an illustration of a simplified side view of a mechanical testing apparatus with a first specimen around a wheel is depicted in accordance with an illustrative embodiment. View 500 is a simplified view of a mechanical testing apparatus. Mechanical testing apparatus 502 is a physical implementation of mechanical testing apparatus 202 of FIG. 2. View 500 of mechanical testing apparatus 502 only depicts wheel 504, platform 506, first specimen 508, and second specimen 510. The other associated components of mechanical testing apparatus 502 such as a motor, a biasing system, bearings, a load shaft, sensors, and other components are not depicted for simplicity.

As depicted, first specimen 508 is secured to wheel 504. First specimen 508 is secured around the entirety of wheel 504. First specimen 508 may be secured using at least one of an adhesive or clamps. Second specimen 510 is secured to platform 506. As depicted, platform 506 is substantially planar.

View 500 also has a superimposed force diagram. The forces acting on first specimen 508 and second specimen 510 are shown in view 500. A static coefficient of friction is the still of rolling friction. The kinetic coefficient of friction is sliding friction of two surfaces past each other. Applied force 512 may be denoted as "F". The static friction coefficient ($\mu_s$) or kinetic friction coefficient ($\mu_k$) is related to applied force 512 through normal force 514. In mechanical testing apparatus 502, the torque is equivalent to applied force 512 times moment arm 516. Mechanical testing apparatus 502 measures torque and converts to friction through prescribing the radius of wheel 504 and normal force 514.

The static friction coefficient ($\mu_s$) and kinetic friction coefficient ($\mu_k$) are determined based on the output from a sensor measuring torque, such as torque transducer 315 of FIG. 3 or torque transducer 245 of FIG. 2. As the motor, such as motor 240 of FIG. 2 or motor 310 of FIG. 3, begins to apply torque, the torque transducer will read an increasing torque. Once wheel 504 begins to slide relative to platform 506, the static coefficient of friction will be represented by the peak of the torque versus time plot. Once the torque application begins to reach steady state the dynamic coefficient of friction will be plotted versus time. These two inputs are used for the inputs into forming models or design guidelines.

Figure 6:
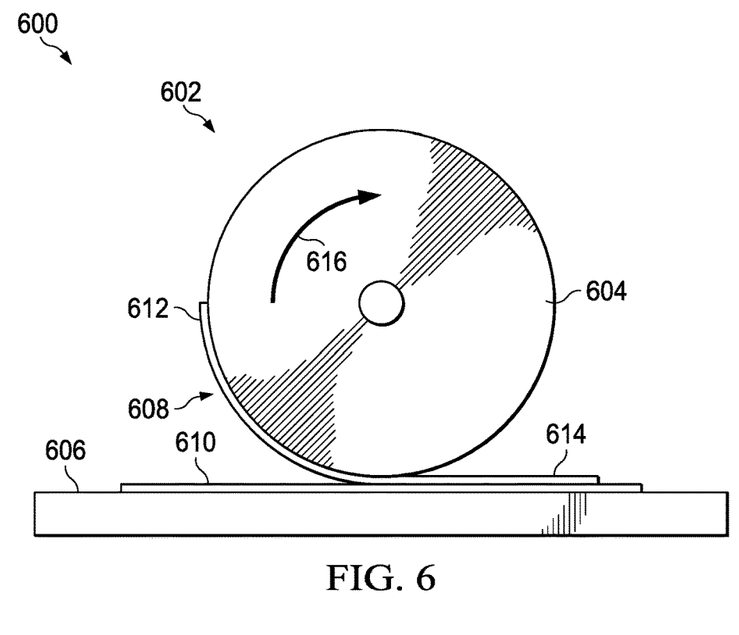
FIG. 6 is an illustration of a simplified side view of a mechanical testing apparatus with a first specimen pulled in tension around a portion of a wheel in accordance with an illustrative embodiment.

Turning now to FIG. 6, an illustration of a simplified side view of a mechanical testing apparatus with a first specimen pulled in tension around a portion of a wheel is depicted in accordance with an illustrative embodiment. View 600 is a simplified view of a mechanical testing apparatus. Mechanical testing apparatus 602 is a physical implementation of mechanical testing apparatus 202 of FIG. 2. View 600 of mechanical testing apparatus 602 only depicts wheel 604, platform 606, first specimen 608, and second specimen 610. The other associated components of mechanical testing apparatus 602 such as a motor, a biasing system, bearings, a load shaft, sensors, and other components are not depicted for simplicity.

As depicted, a portion of first specimen 608 is secured to wheel 604. First portion 612 of first specimen 608 is secured to a portion of wheel 604. First portion 612 of first specimen 608 is secured using at least one of an adhesive or clamps. Second portion 614 of first specimen 608 is loose. As wheel 604 rotates in direction 616, second portion 614 will self-tighten. Second specimen 610 is secured to platform 606. As depicted, platform 606 is substantially planar.

Figure 7:
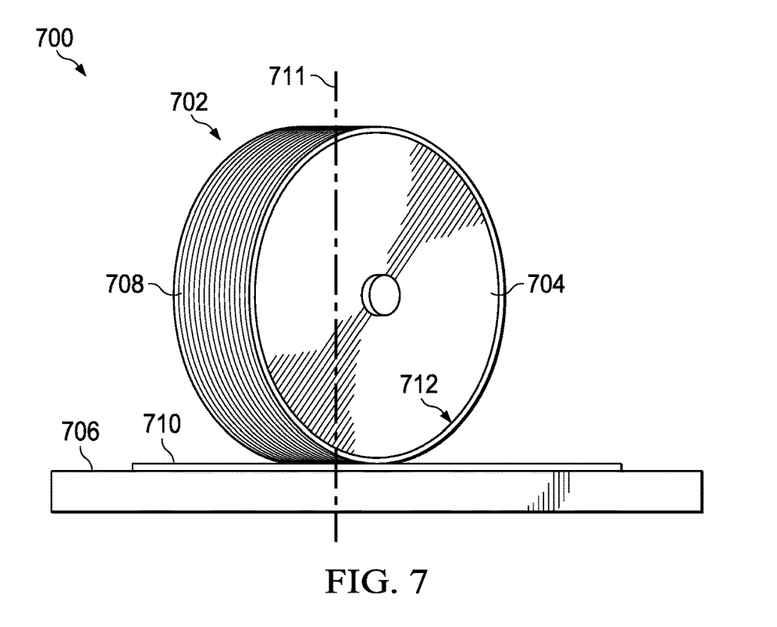
FIG. 7 is an illustration of a simplified side view of a mechanical testing apparatus with the wheel at an angle relative to the second specimen in accordance with an illustrative embodiment.

Turning now to FIG. 7, an illustration of a simplified side view of a mechanical testing apparatus with the wheel at an angle relative to the second specimen is depicted in accordance with an illustrative embodiment. View 700 is a simplified view of a mechanical testing apparatus. Mechanical testing apparatus 702 is a physical implementation of mechanical testing apparatus 202 of FIG. 2. View 700 of mechanical testing apparatus 702 only depicts wheel 704, platform 706, first specimen 708, and second specimen 710. The other associated components of mechanical testing apparatus 702 such as a motor, a biasing system, bearings, a load shaft, sensors, and other components are not depicted for simplicity.

Mechanical testing apparatus 702 may be substantially similar to mechanical testing apparatus 502 of FIG. 5. In some illustrative examples, view 700 may be a view of mechanical testing apparatus 502 with wheel 504 rotated relative to second specimen 710.

As depicted, wheel 704 has been rotated about axis 711 perpendicular to platform 706. More specifically, as depicted, edge 712 of wheel 704 has been rotated into the page such that the relative fiber angle between first specimen 708 and second specimen 710 is changed. By rotating wheel 704, the effective fiber direction of first specimen 708 is changed. Changing the effective fiber direction of first specimen 708 changes the relative fiber angle of second specimen 710 relative to first specimen 708.

Figure 8:
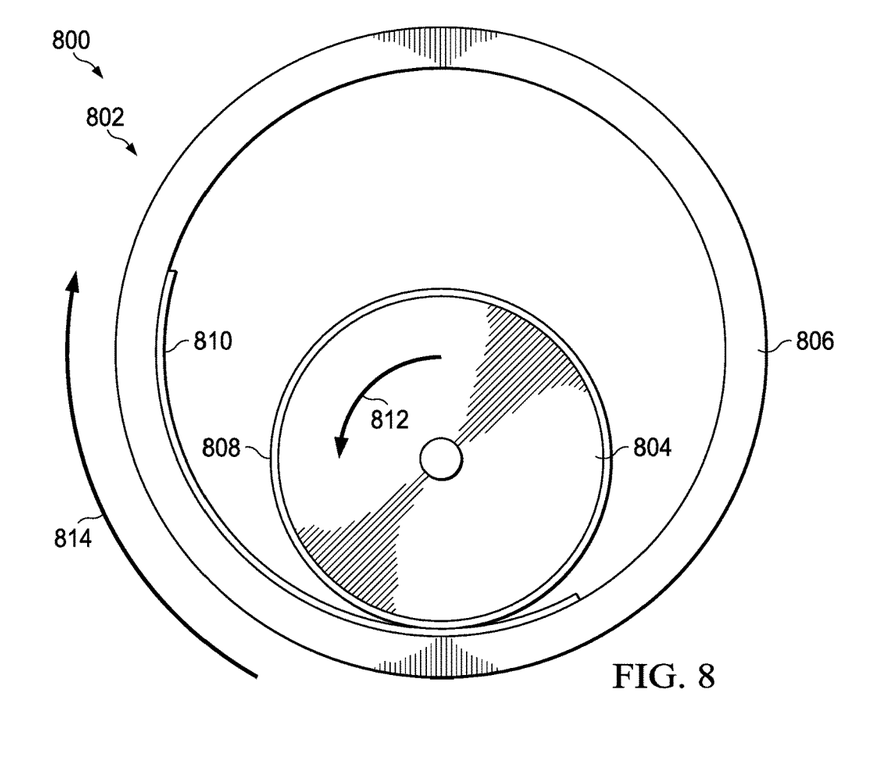
FIG. 8 is an illustration of a simplified side view of a mechanical testing apparatus with a curved platform in accordance with an illustrative embodiment.

Turning now to FIG. 8, an illustration of a simplified side view of a mechanical testing apparatus with a curved platform is depicted in accordance with an illustrative embodiment. View 800 is a simplified view of a mechanical testing apparatus. Mechanical testing apparatus 802 is a physical implementation of mechanical testing apparatus 202 of FIG. 2. View 800 of mechanical testing apparatus 802 only depicts wheel 804, platform 806, first specimen 808, and second specimen 810. The other associated components of mechanical testing apparatus 802 such as a motor, a biasing system, bearings, a load shaft, sensors, and other components are not depicted for simplicity.

As depicted, first specimen 808 is secured to wheel 804. First specimen 808 is secured around the entirety of wheel 804. First specimen 808 may be secured using at least one of an adhesive or clamps.

Second specimen 810 is secured to platform 806. As depicted, platform 806 is curved. Platform 806 is concave towards wheel 804. In some illustrative examples, platform 806 may be referred to as a female platform.

Using wheel 804 that is curved against a curved female surface of platform 806 will create a footprint of wheel 804 against the surface. In a theoretical analysis of FIG. 5, the load is assumed to be a perfect line load across the surface of platform 506 regardless of the presence of a small footprint of wheel 504. In practice, some materials of the specimens may show variability in the validity of this assumption.

By instead applying a designed contact area using wheel 504 and curved surface of platform 506 to create a consistent footprint, the coefficients of friction will be a function of this cross-sectional contact area. Furthermore, mechanical testing apparatus 802 could be used to look at the interlaminar shear strength of composite materials in various states of cure. First specimen 808 on wheel 804 could be cured to the surface of second specimen 810 to create a bondline. This bondline could then be tested in the same mechanical test application and the shear strength of the interlaminar bond would be tested.

To test mechanical properties, wheel 804 will rotate in direction 812 while applying torque to second specimen 810. Due to wheel 804 rotating in direction 812, wheel 804 will move up second specimen 810 in direction 814.

Figure 9:
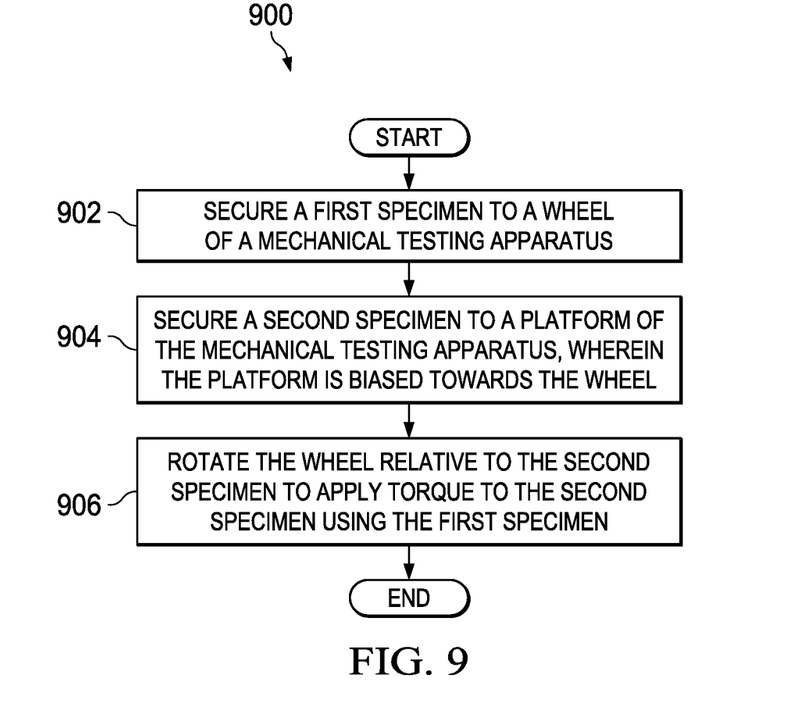
FIG. 9 is an illustration of a flowchart of a method for mechanically testing in accordance with an illustrative embodiment.

Turning now to FIG. 9, an illustration of a flowchart of a method for mechanical testing is depicted in accordance with an illustrative embodiment. Mechanical testing apparatus 202 of FIG. 2 may use method 900 to test first specimen 208 and second specimen 210 of FIG. 2. Mechanical testing apparatus 302 may use method 900 to test first specimen 304 and second specimen 306 of FIG. 3.

Method 900 secures a first specimen to a wheel of a mechanical testing apparatus (operation 902). In some illustrative examples, securing the first specimen to the wheel comprises securing the first specimen to the wheel with at least one of a clamp or an adhesive. In some illustrative examples, the wheel may have a surface texture to create friction between the first specimen and the wheel.

Method 900 secures a second specimen to a platform of the mechanical testing apparatus, wherein the platform is biased towards the wheel (operation 904). In some illustrative examples, the second specimen may be secured to the platform using at least one of a clamp or an adhesive. In some illustrative examples, the second specimen is secured using a picture frame clamping system.

In some illustrative examples, the platform is substantially planar. In other illustrative examples, the platform is curved.

Method 900 rotates the wheel relative to the second specimen to apply torque to the second specimen using the first specimen (operation 906). Afterwards the process terminates.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, method 900 may further comprise indexing the second specimen to an indexing system associated with the platform prior to securing the second specimen with the platform. An effective fiber direction of the second specimen is set using the indexing system. The indexing system may include indicators for indexing the second specimen to a plurality of alternative angles. For example, the indexing system may include indicators for zero degrees, thirty degrees, sixty degrees, ninety degrees, or any other desirable number of fiber angles.

In some illustrative examples, the first specimen and second specimen are composite specimens. In these illustrative examples, method 900 may further comprise taking measurements using a number of sensors; and determining at least one of a friction force, tack of the second specimen, or interply cured strength of the first specimen and the second specimen based on the measurements from the number of sensors. In some illustrative examples, the measurements include at least one of torque measurements, linear displacement measurements, rotational displacement measurements, or temperature measurements.

In some illustrative examples, the first specimen and second specimen are composite specimens. In these illustrative examples, method 900 may further co-cure the first specimen and the second specimen to form a bond between the first specimen and the second specimen prior to applying the rotational force to the wheel. Co-curing includes heating the first specimen and second specimen together. In co-curing, the first specimen and second specimen are cured simultaneously. In this illustrative example, co-curing forms a bond between the first specimen and the second specimen to be tested. The strength of the bond is tested by applying torque using the wheel.

Figure 10:
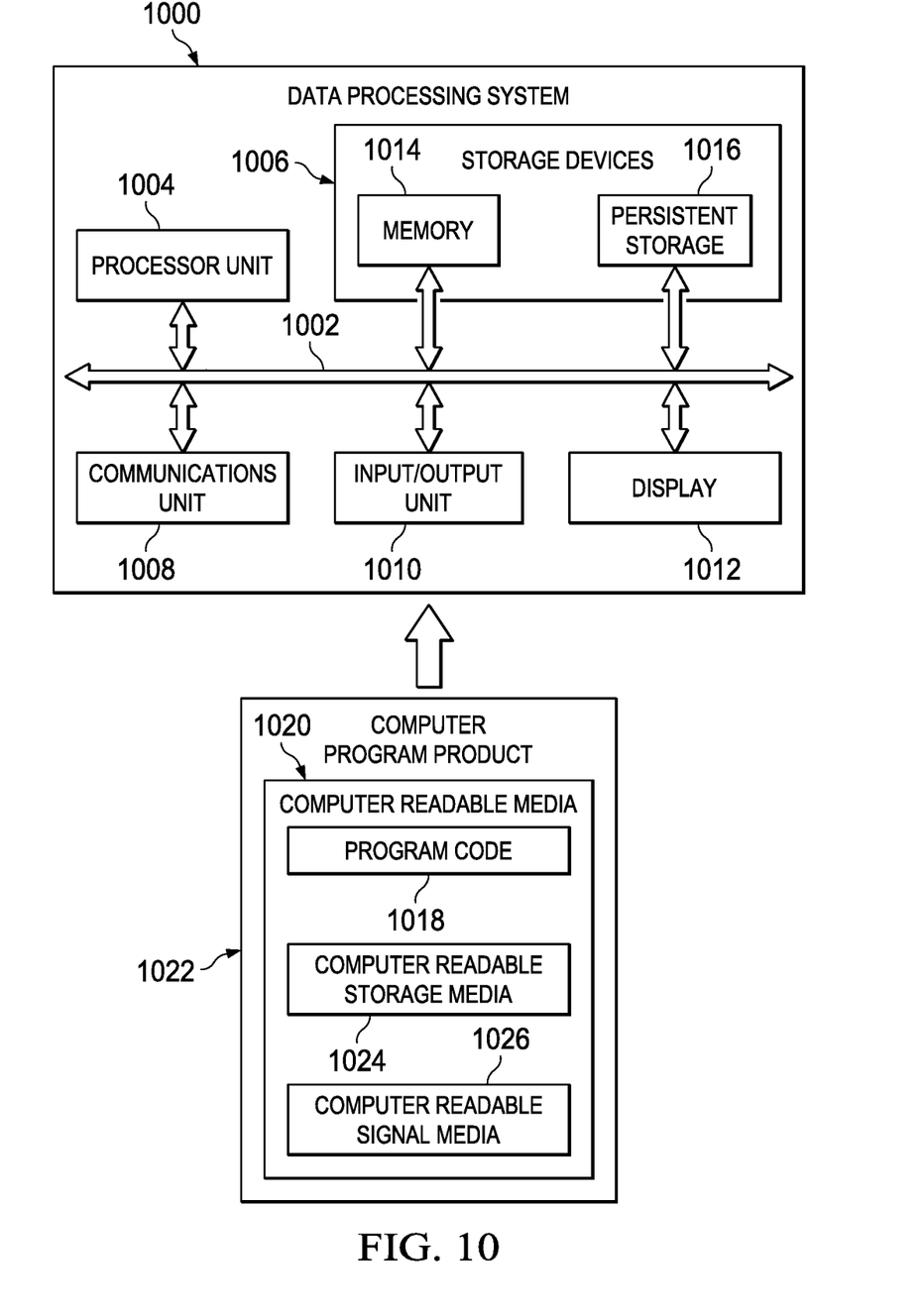
FIG. 10 is an illustration of a data processing system in the form of a block diagram in accordance with an illustrative embodiment.

Turning now to FIG. 10, an illustration of a data processing system in the form of a block diagram is depicted in accordance with an illustrative embodiment. Data processing system 1000 may be used to implement computer system 256 of FIG. 2. Data processing system 1000 may be used to analyze measurements 243 from number of sensors 242 and determine mechanical properties 201 as shown in FIG. 2. As depicted, data processing system 1000 includes communications framework 1002, which provides communications between processor unit 1004, storage devices 1006, communications unit 1008, input/output unit 1010, and display 1012. In some cases, communications framework 1002 may be implemented as a bus system.

Processor unit 1004 is configured to execute instructions for software to perform a number of operations. Processor unit 1004 may comprise a number of processors, a multi-processor core, and/or some other type of processor, depending on the implementation. In some cases, processor unit 1004 may take the form of a hardware unit, such as a circuit system, an application specific integrated circuit (ASIC), a programmable logic device, or some other suitable type of hardware unit.

Instructions for the operating system, applications, and/or programs run by processor unit 1004 may be located in storage devices 1006. Storage devices 1006 may be in communication with processor unit 1004 through communications framework 1002. As used herein, a storage device, also referred to as a computer-readable storage device, is any piece of hardware capable of storing information on a temporary and/or permanent basis. This information may include, but is not limited to, data, program code, and/or other information.

Memory 1014 and persistent storage 1016 are examples of storage devices 1006. Memory 1014 may take the form of, for example, a random access memory or some type of volatile or non-volatile storage device. Persistent storage 1016 may comprise any number of components or devices. For example, persistent storage 1016 may comprise a hard drive, a flash memory drive, a rewritable optical disk, a rewritable magnetic tape, or some combination of the above. The media used by persistent storage 1016 may or may not be removable.

Communications unit 1008 allows data processing system 1000 to communicate with other data processing systems and/or devices. Communications unit 1008 may provide communications using physical and/or wireless communications links.

Input/output unit 1010 allows input to be received from and output to be sent to other devices connected to data processing system 1000. For example, input/output unit 1010 may allow user input to be received through a keyboard, a mouse, and/or some other type of input device. As another example, input/output unit 1010 may allow output to be sent to a printer connected to data processing system 1000.

Display 1012 is configured to display information to a user. Display 1012 may comprise, for example, without limitation, a monitor, a touch screen, a laser display, a holographic display, a virtual display device, and/or some other type of display device.

In this illustrative example, the processes of the different illustrative embodiments may be performed by processor unit 1004 using computer-implemented instructions. These instructions may be referred to as program code, computer usable program code, or computer-readable program code, and may be read and executed by one or more processors in processor unit 1004.

In these examples, program code 1018 is located in a functional form on computer-readable media 1020, which is selectively removable, and may be loaded onto or transferred to data processing system 1000 for execution by processor unit 1004. Program code 1018 and computer-readable media 1020 together form computer program product 1022. In this illustrative example, computer-readable media 1020 may be computer-readable storage media 1024 or computer-readable signal media 1026.

Computer-readable storage media 1024 is a physical or tangible storage device used to store program code 1018 rather than a medium that propagates or transmits program code 1018. Computer-readable storage media 1024 may be, for example, without limitation, an optical or magnetic disk or a persistent storage device that is connected to data processing system 1000.

Alternatively, program code 1018 may be transferred to data processing system 1000 using computer-readable signal media 1026. Computer-readable signal media 1026 may be, for example, a propagated data signal containing program code 1018. This data signal may be an electromagnetic signal, an optical signal, and/or some other type of signal that can be transmitted over physical and/or wireless communications links.

The illustration of data processing system 1000 in FIG. 10 is not meant to provide architectural limitations to the manner in which the illustrative embodiments may be implemented. The different illustrative embodiments may be implemented in a data processing system that includes components in addition to or in place of those illustrated for data processing system 1000. Further, components shown in FIG. 10 may be varied from the illustrative examples shown.

Figure 11:
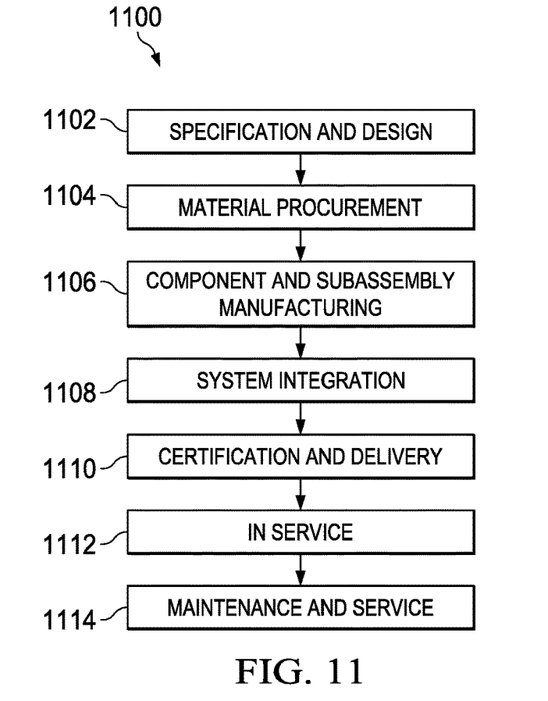
FIG. 11 is an illustration of an aircraft manufacturing and service method in the form of a block diagram in accordance with an illustrative embodiment.
Figure 12:
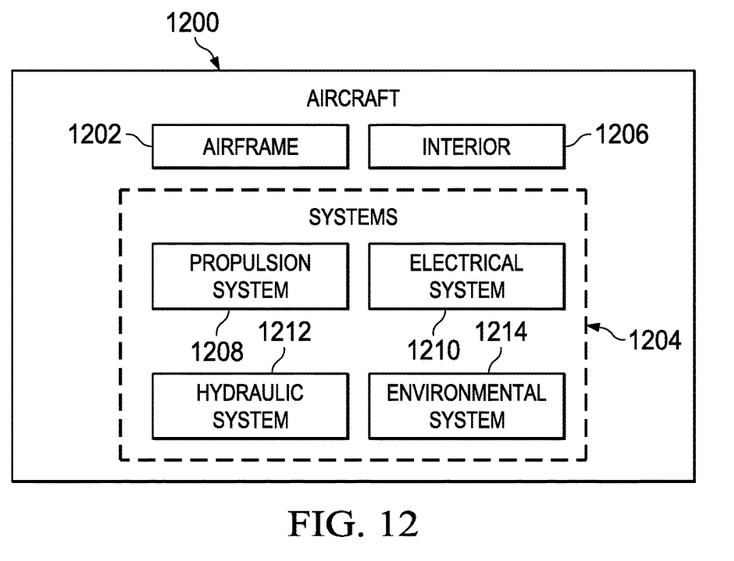
FIG. 12 is an illustration of an aircraft in the form of a block diagram in which an illustrative embodiment may be implemented.

Illustrative embodiments of the present disclosure may be described in the context of aircraft manufacturing and service method 1100 as shown in FIG. 11 and aircraft 1200 as shown in FIG. 12. Turning first to FIG. 11, an illustration of an aircraft manufacturing and service method is depicted in accordance with an illustrative embodiment. During pre-production, aircraft manufacturing and service method 1100 may include specification and design 1102 of aircraft 1200 in FIG. 12 and material procurement 1104.

During production, component and subassembly manufacturing 1106 and system integration 1108 of aircraft 1200 take place. Thereafter, aircraft 1200 may go through certification and delivery 1110 in order to be placed in service 1112. While in service 1112 by a customer, aircraft 1200 is scheduled for routine maintenance and service 1114, which may include modification, reconfiguration, refurbishment, and other maintenance or service.

Each of the processes of aircraft manufacturing and service method 1100 may be performed or carried out by a system integrator, a third party, and/or an operator. In these examples, the operator may be a customer. For the purposes of this description, a system integrator may include, without limitation, any number of aircraft manufacturers or major-system subcontractors; a third party may include, without limitation, any number of vendors, subcontractors, or suppliers; and an operator may be an airline, a leasing company, a military entity, a service organization, and so on.

With reference now to FIG. 12, an illustration of an aircraft is depicted in which an illustrative embodiment may be implemented. In this example, aircraft 1200 is produced by aircraft manufacturing and service method 1100 in FIG. 11 and may include airframe 1202 with a plurality of systems 1204 and interior 1206. Examples of systems 1204 include one or more of propulsion system 1208, electrical system 1210, hydraulic system 1212, and environmental system 1214. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1100. One or more illustrative embodiments may be used during component and subassembly manufacturing 1106 of FIG. 11. For example, mechanical testing apparatus 202 of FIG. 2 may be used to test material characteristics prior to forming a part from the material during component and subassembly manufacturing 1106. Further, mechanical testing apparatus 202 of FIG. 2 may be used to test material characteristics for replacement parts during maintenance and service 1114 of FIG. 11.

The disclosure measures the static and dynamic coefficient of friction between plies in a single test under a single set up. The disclosure presents a new fixture for variable controlled tack, shear, and sliding friction. Variables for testing include temperature, rate, fiber orientation, ply angle, load/pressure, compaction, and dynamic versus static tack. The addition of heat allows for measurement of the changing viscosity of the matrix and fiber together. Using the presented apparatus, one ply of material can be tested in a number of off-axis orientations.

Using the presented apparatus, tooling material effects may be evaluated as well as interply tack and shear effects. The materials of the mounting wheel and the platform have an effect on the resulting friction response. When testing similar materials against each other there is a cohesive polymer to polymer attraction between like molecules. When testing dissimilar materials, for example metal to prepreg, there is a mechanical adhesion driving the friction due to mechanical entanglement of the polymer and the surface roughness of the mounting material. With this information, design studies can be run to understand the friction against different manufacturing tooling materials as well as different types of resin chemistries and fiber forms relative to each other.

The presented apparatus can perform a heated test. In some illustrative examples, the presented apparatus heats a contact area with an electric resistive heater. The heating may be performed with manual or PID temperature control. The tests may run material through controlled forming or cure cycle temperature ranges.

The presented apparatus will apply pressure on the sample based on spring loads or a linear actuator. Traditional test methods rely heavily on a load frame based test method which holds the sample in one direction. In the presented apparatus, the specimen is indexed and mounted to the bottom plate for off-axis measurements. For example, the sample may be mounted relative to the bottom plate for off-axis measurements.

Currently, building process models for forming operations requires numerous materials and process characterization inputs in order to analyze the resulting formed part. These characterization approaches have the potential to offer both modeling inputs as well as design guidelines for forming operations. The key parameters to measure for forming operations include fabric locking angle, intra-ply shear, inter-ply slipping/friction, and ply bending. All of these parameters have multiple testing approaches and the test standards have not been developed for these characterizations.

Additionally, of these test parameters, the inter-ply properties are particularly difficult to measure. The current state of testing is the double-lap shear test and it has many variations. However, the double lap shear test is a cross sectional area dependent test. Thus, if the cross-sectional contact area changes, the measured force response will also change. Also, the double-lap shear test has difficulty capturing the effects of off-axis plies. The test is a tensile test. If zero degree plies are aligned with zero degree plies in a double lap shear test, then the tensile load is transferred through the fibers and the sliding force is measured. However, if zero degree plies are aligned with ninety degree plies, only some of the fibers are aligned in the loading direction and the ninety-degree plies separate at the matrix.

This new characterization fixture solves the need to obtain rapid and repeatable testing results for inter-ply properties. This would include the static coefficient of friction as well as the dynamic coefficient of friction between composite material plies in a single test. Additionally, the off-axis measurements could be rapidly measured by indexing the bottom plate of material across a fiber wheel. A new testing fixture is proposed to initially add robustness to the characterization of inter-ply friction properties. This would include the static coefficient of friction as well as the dynamic coefficient of friction in a single test. Additionally, the off-axis measurements could be rapidly measured and the test is not cross-sectionally dependent.

The inter-ply characterization fixture would consist of a fiber wheel mounted to a drive shaft. The drive shaft would be connected to a bearing in line with the torque transducer. The fiber wheel would be mounted with a spring-loaded cog system or threaded on for quick test sample interchanges. The fiber wheel would have prepreg bonded or clamped to a rough or textured wheel surface. Two test method variations would include a fiber prepreg tape wrapped around the wheel completely and a second variation would be a tape clamped to the wheel on one side and pulled around the wheel in continuous tension. The fiber plate would be indexed to the orientations of interest and loaded against the fiber wheel with a normal load source (i.e. pneumatic, linear actuator, threaded rod, or spring). The fibers would be clamped to the surface of the fiber plate with a spring-loaded picture frame clamping mechanism that surrounds the fiber prepreg square. The mechanical system would be enclosed in a framed structure initially composed of t-slot aluminum.

The electrical system would consist of a few components. The motor would be an electric torque source able to output the required torque to induce initial sliding of the fiber wheel on the fiber plate. The motor may need to be coupled with a motor encoder to detect the position of the fiber wheel in relation to the applied torque. The torque transducer will need to be appropriately sized for the expected torque ranges. The expected torque ranges will be a function of temperature and some preliminary tests may need to be run to measure the expected break away torque. A load cell would likely be implemented underneath the fiber plate in order to measure the applied normal load and any change to the normal load with the fiber wheel rotation.

A motor controller for the electric motor, as well as a data acquisition unit for the torque transducer, load cell, and any thermocouples would be required as well. This would be the key to calculating the coefficient of friction between plies as sliding takes place.

The heating system would initially consist of an electric resistive heater underneath the fiber plate. This could then be augmented with electrical resistive heaters in the fiber wheel. A third option would enclose the mechanical system in an environmental chamber for a variety of environmental conditions of interest.

An inter-ply characterization fixture is disclosed. The fixture comprises an indexing fiber plate fitted with a resistive heater underneath the fiber plate, a torque transducer, a fiber wheel, wherein the fiber wheel is mounted to a drive shaft in communication with a bearing in line with the torque transducer, an electric torque source, a torque source controller, and a data acquisition unit in communication with the torque transducer, load cell, and any thermocouples, wherein the data acquisition unit provides inputs for calculating a coefficient of friction between plies as sliding takes place. The fiber plate is indexed to orientations of interest and loaded against the fiber wheel with a normal load source. The normal load source is one of a pneumatic, a linear actuator, a threaded rod, or a spring.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A mechanical testing apparatus comprising:
   a wheel configured to hold a first specimen and rotate relative to a second specimen to apply torque to the second specimen using the first specimen; and
   a platform biased towards the wheel and configured to hold the second specimen.

2. The mechanical testing apparatus of claim 1 further comprising:
   a sensor associated with the wheel configured to measure a torque applied by the wheel.

3. The mechanical testing apparatus of claim 1, wherein the first specimen and the second specimen are composite specimens.

4. The mechanical testing apparatus of claim 3 further comprising:
   an indexing system associated with the platform, wherein a fiber angle of the second specimen relative to the first specimen is set using the indexing system.

5. The mechanical testing apparatus of claim 1, wherein the platform is curved.

6. The mechanical testing apparatus of claim 1, wherein the platform is substantially planar.

7. The mechanical testing apparatus of claim 1 further comprising:
   the first specimen, wherein the first specimen is associated with the wheel by at least one of a clamp or an adhesive.

8. The mechanical testing apparatus of claim 7, wherein only a portion of the first specimen is secured to the wheel.

9. The mechanical testing apparatus of claim 1 further comprising:
   a number of sensors configured to measure at least one of a linear displacement of the platform, a rotational displacement of the wheel, or a temperature of the platform.

10. A mechanical testing method comprising:
    securing a first specimen to a wheel of a mechanical testing apparatus;
    securing a second specimen to a platform of the mechanical testing apparatus, wherein the platform is biased towards the wheel; and
    rotating the wheel relative to the second specimen to apply torque to the second specimen using the first specimen.

11. The mechanical testing method of claim 10, wherein securing the first specimen to the wheel comprises securing the first specimen to the wheel with at least one of a clamp or an adhesive.

12. The mechanical testing method of claim 10 further comprising:
    indexing the second specimen to an indexing system associated with the platform prior to securing the second specimen to the platform.

13. The mechanical testing method of claim 10, wherein the first specimen and second specimen are composite specimens, the method further comprising:
    taking measurements using a number of sensors; and
    determining at least one of a friction force, a tack of the second specimen, or an interply cured strength of the first specimen and the second specimen based on the measurements from the number of sensors.

14. The mechanical testing method of claim 13, wherein the measurements include at least one of torque measurements, linear displacement measurements, rotational displacement measurements, or temperature measurements.

15. The mechanical testing method of claim 10, wherein the first specimen and the second specimen are composite specimens, the method further comprising:
co-curing the first specimen and the second specimen to form a bond between the first specimen and the second specimen prior to applying rotational force to the wheel.

16. A system comprising:
a mechanical testing apparatus comprising:
  a wheel,
  a motor connected to the wheel and configured to apply a rotational force to the wheel,
  a platform biased towards the wheel by a biasing member; and
  a number of sensors configured to measure at least one of a temperature, a torque, a linear translation, a rotational translation, or an applied load;
a first specimen secured to the wheel of the mechanical testing apparatus; and
a second specimen secured to the platform of the mechanical testing apparatus.

17. The system of claim 16, wherein the platform is curved.

18. The system of claim 16, wherein the first specimen is a first composite specimen, wherein the second specimen is a second composite specimen, and wherein an effective fiber direction of the second specimen is a result of indexing of the second specimen relative to the platform.

19. The system of claim 16, wherein the biasing member is a spring.

20. The system of claim 16, wherein the wheel is an interchangeable wheel.

\* \* \* \* \*